United States Patent
Matz et al.

(10) Patent No.: US 10,682,051 B2
(45) Date of Patent: Jun. 16, 2020

(54) SURGICAL SYSTEM HAVING AN OCT DEVICE

(71) Applicant: Carl Zeiss Meditec AG, Jena (DE)

(72) Inventors: Holger Matz, Unterschneidheim (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 391 days.

(21) Appl. No.: 15/481,381

(22) Filed: Apr. 6, 2017

(65) Prior Publication Data
US 2017/0209042 A1  Jul. 27, 2017

Related U.S. Application Data

(63) Continuation of application No. PCT/EP2015/072962, filed on Oct. 5, 2015.

(30) Foreign Application Priority Data

Oct. 6, 2014 (DE) .......................... 10 2014 220 198
Nov. 5, 2014 (DE) .......................... 10 2014 222 629

(51) Int. Cl.
*A61B 3/10* (2006.01)
*A61F 9/007* (2006.01)
(Continued)

(52) U.S. Cl.
CPC ............ *A61B 3/102* (2013.01); *A61B 3/0025* (2013.01); *A61B 3/0041* (2013.01); *A61B 3/13* (2013.01);
(Continued)

(58) Field of Classification Search
CPC .... A61B 2034/2055; A61B 2034/2065; A61B 2090/3735; A61B 34/20; A61B 3/0025;
(Continued)

(56) References Cited

U.S. PATENT DOCUMENTS 5,321,501 A  6/1994 Swanson et al.
5,795,295 A  8/1998 Hellmuth et al.
(Continued)

FOREIGN PATENT DOCUMENTS

DE  10 2009 040 687 A1  3/2011

OTHER PUBLICATIONS

International Search Report dated Jan. 11, 2016 of international application PCT/EP2015/072962 on which this application is based.
(Continued)

*Primary Examiner* — Imani N Hayman
(74) *Attorney, Agent, or Firm* — Walter Ottesen, P.A.

(57) ABSTRACT

A system for performing a surgical procedure includes an OCT unit for scanning an object region volume with an OCT scanning beam and a control unit for setting the position of the object region volume. A surgical instrument having an effective section is arrangeable in an object region of the object region volume and is localizable in the object region volume with the OCT unit. A computer unit has a first computer program for determining the position of the effective section by processing scan information obtained by scanning the object region volume and a second computer program compares the scan information to reference data and provides a set value for the position of the effective section. The second computer program determines deviation information as to the spatial deviation of the effective section from the set value.

16 Claims, 7 Drawing Sheets

(51) Int. Cl.
    *A61B 3/13*     (2006.01)
    *A61B 34/20*    (2016.01)
    *A61B 90/20*    (2016.01)
    *G02B 21/00*    (2006.01)
    *A61B 90/00*    (2016.01)
    *A61B 3/00*     (2006.01)
    *A61F 9/00*     (2006.01)
    *A61F 9/008*    (2006.01)

(52) U.S. Cl.
    CPC .............. *A61B 34/20* (2016.02); *A61B 90/20* (2016.02); *A61B 90/37* (2016.02); *A61F 9/0017* (2013.01); *A61F 9/00736* (2013.01); *G02B 21/0012* (2013.01); *A61B 2034/2055* (2016.02); *A61B 2034/2065* (2016.02); *A61B 2090/3735* (2016.02); *A61F 9/0008* (2013.01); *A61F 2009/00851* (2013.01)

(58) Field of Classification Search
    CPC ......... A61B 3/0041; A61B 3/102; A61B 3/13; A61B 90/20; A61B 90/37; A61F 2009/00851; A61F 9/0008; A61F 9/0017; A61F 9/00736; G02B 21/0012
    See application file for complete search history.

(56) References Cited

U.S. PATENT DOCUMENTS

| | | |
|---|---|---|
| 7,477,764 B2 | 1/2009 | Haisch |
| 8,740,380 B2 | 6/2014 | Wilzbach et al. |
| 9,127,929 B2 | 9/2015 | Siercks et al. |
| 9,554,701 B2 | 1/2017 | Wilzbach et al. |
| 2009/0015842 A1 | 1/2009 | Leitgeb et al. |
| 2011/0201939 A1 | 8/2011 | Hubschman et al. |
| 2012/0184846 A1 | 7/2012 | Izatt et al. |
| 2012/0226150 A1 | 9/2012 | Balicki et al. |
| 2014/0211155 A1 | 7/2014 | Sakagawa et al. |
| 2015/0342698 A1 | 12/2015 | Eslami et al. |

OTHER PUBLICATIONS

Translation and Written Opinion of the International Searching Authority dated Jan. 11, 2016 of international application PCT/EP2015/072962 on which this application is based.

International Preliminary Report on Patentability dated Apr. 20, 2017 of international application PCT/EP2015/072962 on which this application is based.

A. Ehnes: Entwicklung eines Schichtsegmentierungsalgorithmus zur automatischen Analyse von individuellen Netzhautschichten in optischen Kohaerenztomographie-B-Scans, Dissertation, Giessen 2013, chapter 3, pp. 45 to 82, available at http://docplayerorg/3251932-Inauguraldissertation-zur-erlangung-des-grades-eines-doktors-der-humanbiologie-des-fachbereichs-medizin-der-justusliebig-universitaet-giessen.html.

SURGICAL SYSTEM HAVING AN OCT DEVICE

CROSS REFERENCE TO RELATED APPLICATION

This application is a continuation application of international patent application PCT/EP2015/072962, filed Oct. 5, 2015, designating the United States and claiming priority from German application 10 2014 220 198.5, filed Oct. 6, 2014, and German application 10 2014 222 629.5, filed Nov. 5, 2014, and the entire content of the above applications is incorporated herein by reference.

FIELD OF THE INVENTION

The invention relates to a surgical system comprising an OCT device for scanning an object region volume arranged in an object region using an OCT scanning beam and comprising a device for setting the position (P) of the object region volume scanned by the OCT scanning beam in the object region. Moreover, the invention relates to a method for operating a surgical instrument, and a computer program. The term "OCT" is an abbreviation for "optical coherence tomography."

BACKGROUND OF THE INVENTION

U.S. Pat. No. 5,795,295 has disclosed a surgical system of the type set forth above. This surgical system is embodied as a surgical microscope and comprises an OCT device which produces an OCT scanning beam path defined by short coherent laser radiation. The OCT device contains an analysis unit for evaluating interference signals. It comprises a device for scanning the OCT scanning beam path, comprising two scanning mirrors which may be adjusted about two movement axes. The OCT scanning beam path in the surgical microscope is coupled into the illumination beam path of the surgical microscope by way of a splitter mirror. With the latter, it is deflected through the microscope main objective to an object region in a patient eye.

United States patent application 2012/0184846 A1 discloses a surgical microscope system having an OCT-device which makes possible to update the OCT-image of the spatial position of a surgical instrument in a surgical region.

DE 2009 040 687 A1 discloses an OCT-device having a displaceable measurement probe which makes it possible to determine location resolved structural information in an object region.

SUMMARY OF THE INVENTION

It is an object of the invention to simplify the handling of a surgical instrument in an operating field for a surgeon.

A surgical system according to the invention contains an OCT device for scanning an object region volume arranged in an object region, for example, by means of an A-scan, B-scan or C-scan, using an OCT scanning beam and comprising a device for setting the position (P) of the object region volume scanned by the OCT scanning beam in the object region. The surgical system comprises a surgical instrument which comprises an effective portion which is arrangeable in the object region and localizable in the object region volume using the OCT device. The surgical system according to the invention contains a computing unit connected to the OCT device, comprising a computer program for ascertaining the position of the effective portion in the scanned object region volume by processing scanning information obtained by the OCT device by scanning the object region volume.

A surgical system according to the invention therefore facilitates reliable localization of the surgical instrument in a patient eye, even if the surgical instrument consists in part of a material which is transparent to visible light or if this instrument is covered by body tissue in the patient eye. The OCT device in the surgical system according to the invention serves, in particular, to measure and represent structures of body tissue in an operating region in a non-invasive manner by means of optical coherence tomography (OCT). Here, as an optical imaging method, optical coherence tomography facilitates, in particular, the production of slice or volume images of the body tissue with micrometer resolution.

An OCT device in a surgical system according to the invention comprises a source for temporally incoherent and spatially coherent laser light with a coherence length $I_c$, which is fed to a sample beam path and a reference beam path. The sample beam path is directed to the tissue to be examined. The laser light which is radiated back into the sample beam path on account of scattering centers in the tissue has laser light from the reference beam path superposed thereon in the OCT device. An interference signal arises as a result of this superposition. The position of scattering centers for the laser radiation in the examined tissue may be determined from this interference signal.

In particular, an OCT device in a surgical system according to the invention may be configured as a "time domain OCT" or as a "Fourier domain OCT".

By way of example, the configuration of a "time domain OCT" is described in column 5, line 40—column 11, line 10 in U.S. Pat. No. 5,321,501 on the basis of FIG. 1A. In such a system, the optical path length of the reference beam path is continuously varied by way of a quickly moving reference mirror. The light from the sample beam path and reference beam path is superimposed on a photodetector. An interference signal arises on the photodetector if the optical path lengths of sample beam path and reference beam path correspond.

By way of example, a "Fourier domain OCT" is explained in United States patent application publication 2009/0015842 A1. In order to measure the optical path length of a sample beam path, light from a reference beam path is once again superposed on light from the sample beam path. However, in contrast to a "time domain OCT", the light from sample and reference beam path is not fed directly to a detector for the purposes of measuring the optical path length of the sample beam path but initially spectrally decomposed by means of a spectrometer. The spectral intensity of the superposed signal of a sample and reference beam path produced thus is then captured by a detector. Once again, the optical path length of the sample beam path may be ascertained by evaluating the detector signal.

An advantageous configuration of the invention provides for volume data of a tissue area in an object region to be evaluated on an ongoing basis by means of the OCT device in order to determine data for a target area therewith. Here, the position data of the surgical instrument may also be determined on an ongoing basis by means of the OCT device in order then to calculate the distance between the target area and the position of the instrument from the data of the target area and the position data of the instrument. An advantageous configuration of the invention may moreover provide for the determination of the data of the target area to be calculated from the volume data, for example by virtue of segmenting tissue structures and/or tissue layers. It is also an idea of the invention that the surgical instrument may be a hypodermic needle. In particular, it is an idea of the invention that the effective portion of the surgical instrument comprises a capillary with an opening for discharging medium into the object region. This allows the surgical system, in particular, to assist with a stem cell therapy for treating dry age-related macular degeneration (AMD).

Dry AMD is the most common form of age-related macular degeneration. This disorder occurs in various stages. In an early phase of dry age-related AMD, yellow accumulations arise in the background of the afflicted eye, the accumulations being referred to as drusen. These drusen arise as metabolic end products in the so-called Bruch's membrane, which is situated below the retinal pigment epithelium (RPE). These drusen vary in size and number, and are considered to be a natural part of the aging process of the eye.

Over time, the dry AMD may develop to form either an advanced form of dry AMD or wet AMD. In the advanced form of dry AMD, the function of the light-sensitive cells and the surrounding tissue in the macula deteriorates. At the same time, the number and size of the drusen increases progressively. This then leads to significant impairment of the visual faculty of a person suffering from AMD.

For the purposes of treating the dry AMD, a surgical system according to the invention allows a surgeon to inject stem cells at selected positions on the retina by means of a surgical instrument, this surgical instrument having an effective portion, the position of which is visualized for the surgeon when discharging the stem cells. Already damaged retinal pigment epithelium (RPE) with the photoreceptors arranged thereon may become healthy again at the points of the retina at which stem cells are discharged. Moreover, the drusen reformation is reduced at these points.

By virtue of the effective portion of the surgical instrument having a capillary with an opening for discharging medium into the object region, the surgical system, in principle, also facilitates the precise detachment of corneal tissue during deep anterior lamellar keratoplasty (DALK) surgery. During this operation, corneal tissue of the patient is replaced by donor tissue. By virtue of Descemet's membrane being completely exposed in the process, an ideal optical contact between receiver tissue and donor tissue may be ensured.

In a DALK operation, air is injected into the stroma just in front of Descemet's membrane using a surgical instrument in the form of a thin needle. The air bubble ("big bubble") produced hereby causes the detachment of tissue. This tissue may easily be removed and it is then possible to sew on appropriate donor material in the regions of the cornea with detached tissue.

Using a surgical system according to the invention, the exact spatial position of the effective portion of the surgical instrument used for injecting the "big bubble" may be visualized in the corneal tissue during the DALK operation.

A preferred configuration of the invention provides for the effective portion of the surgical instrument to consist at least in part of a material transparent to visible light. This renders it possible to ensure that the effective portion of the surgical instrument does not cover portions of a patient eye, and so these are visible to the surgeon.

In principle, the effective portion of a surgical instrument may also consist of a material that is opaque to visible light, for example, stainless steel. However, what must then be accepted is that the surgical instrument covers structures in an object region.

It is advantageous, if a marker, which is localizable by the OCT scanning beam, is arranged in the effective portion of the surgical instrument. By way of example, this marker may be constructed from a material mixed with iron or carbon nanoparticles, the material being transparent to visible light but at least partly absorbing or scattering on account of the nanoparticles. By way of example, this measure facilitates the ability to calculate the position of the instrument tip from a known geometry of the instrument and a marker signal.

It is also advantageous if a tracking operating mode may be set using the computer program in the computing unit by virtue of the OCT device continuously obtaining control signals with information in respect of the ascertained position of the effective portion by the computing unit for the purposes of tracking, that is, constantly ascertaining the spatial position of, the effective portion. A further advantageous configuration of the invention in this case provides for scanning of object region volumes in the object region to be realized by means of different scanning patterns for the purposes of determining the position of the effective portion of the surgical instrument on the one hand and for capturing the structures of body tissue on the other hand. By way of example, it is possible to scan an object region volume by means of the OCT scanning beam with a lower rate, for example, only once per second, and, in contrast thereto, scan the effective portion of the surgical instrument 10 or even 100 times per second. In this way, the position of the effective portion of the surgical instrument may be displayed to a surgeon in real time and with a high resolution within the structures of the body tissue, the location of which may change due to patient movements in the object region at a slow pace when body tissue is moved in relation to the movement of the surgical instrument.

The surgical system preferably has means for predetermining an intended value for the position of the effective portion in the object region volume. The means for predetermining the intended value may contain, in particular, a computer program for comparing the scanning information in relation to the object region volume, obtained by the OCT device, to reference data in order thereby to determine a target area for the effective portion of the surgical instrument, in particular by means of image evaluation. By way of example, algorithms for the slice segmentation of the retina of a patient eye may be used for determining the target area, as are described in chapter 3, pages 45 to 82 in A. Ehnes, "Entwicklung eines Schichtsegmentierungsalgorithmus zur automatischen Analyse von individuellen Netzhautschichten in optischen Kohärenztomographie—B-Scans", Dissertation, University of Giessen (2013), the entirety of which is referred to herewith, with the explanations made therein also being included in the description of this invention. In particular, these reference data may comprise diagnostic data obtained pre-surgery, for example by means of an x-ray or MRI system.

It is advantageous if the means for predetermining the intended value for the position of the effective portion in the object region volume comprise an input interface for manually entering the intended value. This allows a surgeon to precisely set the intended value for the position of the effective portion of the surgical instrument in the object region volume on the surgical system during surgery.

The computer program in the surgical system is preferably configured for ascertaining deviation information about the spatial deviation of the effective portion from the intended value. The surgical system may also contain means for providing a position indication signal depending on the ascertained deviation of the effective portion from the intended value. It is advantageous if these means provide the position indication signal if a norm of the deviation of the effective portion from the predeterminable intended value drops below a defined threshold. Preferably, this threshold is adjustable. In particular, the position indication signal may be an acoustic and/or an optical and/or a haptic indication signal, such as, for example, a vibrating handle piece of the surgical instrument.

Expediently, from the deviation information, the computer program generates a control signal, supplied to the surgical instrument, for triggering an instrument function if a trigger criterion, such as, for example, a certain penetration depth of the effective portion of the surgical instrument into body tissue or a specific position of the effective portion of the surgical instrument in the object region, is present. By way of example, this control signal may trigger the injection of stem cells or the provision of air if a certain deviation is present.

An idea of the invention is also to visualize the position of the effective portion of the surgical instrument in the object region for an observer, for example, a surgeon, and, to this end, segment, in particular, structures of the body tissue captured by means of the OCT device, as described, for example, in chapter 3, pages 45 to 82 in A. Ehnes, "Entwicklung eines Schichtsegmentierungsalgorithmus zur automatischen Analyse von individuellen Netzhautschichten in optischen Kohärenztomographie—B-Scans", Dissertation, University of Giessen (2013). There advantageously is a surgical microscope for providing an image of the object region with magnification in the surgical system. Here, the position indication signal may be superimposed onto an observation beam path of the microscope, for example with the aid of mirroring-in data.

The method according to the invention comprises at least the steps of arranging an effective portion of a surgical instrument in an object region, capturing the object region with the effective portion of the surgical instrument arranged therein with the aid of an OCT scanning beam and ascertaining the position of the effective portion in the scanned object region volume. In particular, the method according to the invention may also comprise a step of discharging medium with the surgical instrument.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
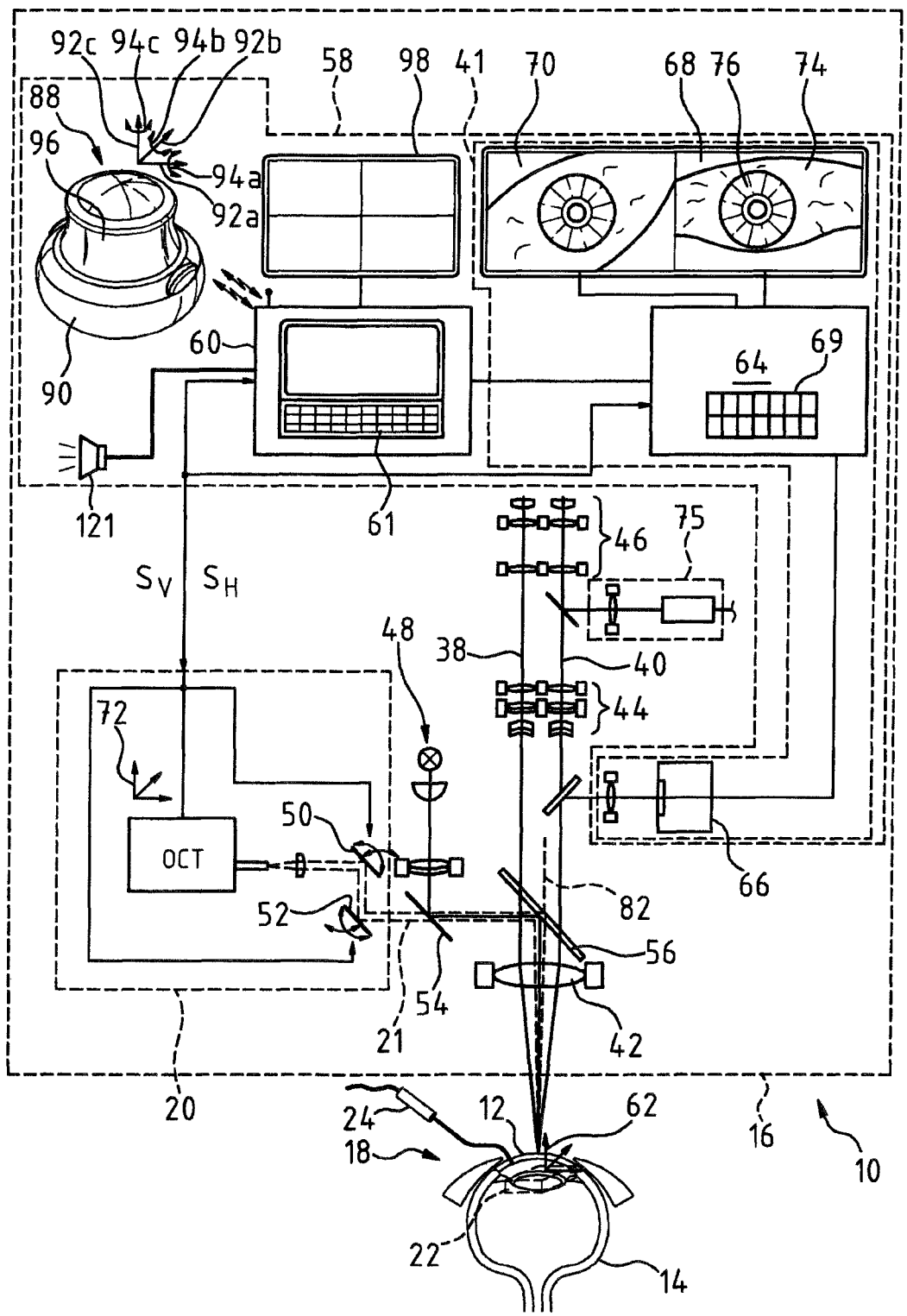
FIG. 1 is a schematic of a first surgical system for ophthalmic surgery, comprising a surgical microscope and OCT device, as well as a surgical instrument.

The surgical system 10 shown in FIG. 1 serves for deep anterior lamellar keratoplasty in ophthalmology. In this operation, all tissue layers of the cornea 12 of a patient eye 14 on which endothelial cells are situated are removed, with the exception of Descemet's membrane. The surgical system 10 contains the surgical microscope 16 for visualizing the object region 18 with magnification. The surgical system 10 comprises an OCT device 20 which provides an OCT scanning beam 21 for scanning the object region volume 22 with an A-, B- and C-scan at the patient eye 14, as described e.g in chapter 3, pages 45 to 82 in A. Ehnes, "Entwicklung eines Schichtsegmentierungsalgorithmus zur automatischen Analyse von individuellen Netzhautschichten in optischen Kohärenztomographie—B-Scans", Dissertation, University of Giessen (2013).

A hypodermic needle, by means of which an air bubble may be injected into the cornea 12 of the patient eye 14 in order thereby to separate Descemet's membrane from the remainder of the cornea 12, exists in the surgical system 10 as a surgical instrument 24. Separating Descemet's membrane from the remainder of the cornea 12 allows the upper layers of the cornea to be removed in order subsequently to sew on donor material.

Figure 2:
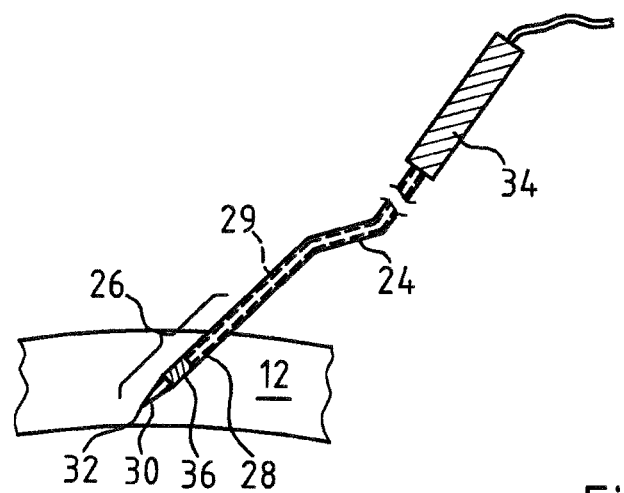
FIG. 2 shows a partial view of the surgical instrument.

FIG. 2 is an enlarged partial view of the surgical instrument 24. The surgical instrument 24 embodied as a hypodermic needle has an effective portion 26 at a needle body 28, which is extended in a longitudinal direction, with a capillary 29 formed therein, the capillary having an opening 32 at the tip 30 of the needle body 28. The surgical instrument 24 comprises a handle piece 34, through which sterile nitrogen gas may be introduced into the needle body 28 from a gas volume (not depicted here). The needle body 28 consists of a material transparent to visible light, for example, mineral glass or PTFE. A marker 36 is formed on the needle body 28 in the vicinity of the tip 30. The marker 36 is a region of the capillary 29 to which nanoparticles, for example, made of iron or carbon, have been added, the nanoparticles partly absorbing the OCT scanning beam 21. The marker 36 is transparent to visible light. However, the spatial position of the marker 36 may be captured using the OCT scanning beam 21 of the OCT device 20. The configuration of such a marker has been described in detail in U.S. Pat. Nos. 8,740,380 and 9,554,701, the entire contents of which are incorporated herein by reference.

The surgical microscope 16 comprises a stereoscopic observation beam path 38, 40, which facilitates the examination of the patient eye 14 through a microscope main objective 42 in the object region 18. The surgical microscope 16 further comprises a zoom system 44 and an eyepiece 46. The surgical microscope also comprises an illumination device 48 which illuminates the object region 18 with illumination light through the microscope main objective 42 for the purposes of stereoscopically visualizing the patient eye 14 in the eyepiece 46.

The OCT device 20 provides the OCT scanning beam 21 with short coherent light, which is guided through the microscope main objective 42 to the object region 18 in an object region volume 22 by way of adjustable scanning mirrors 50, 52 and beam splitters 54 and 56. The light of the OCT scanning beam 21 scattered in the object region volume 22 returns at least in part to the OCT device 20 via the same light path. Then, the light path of the scanning light is compared in the OCT device 20 to a reference path. Using this, it is possible to capture the precise position of scattering centers in the object region 18, in particular the position of optically effective areas, with an accuracy which corresponds to the coherence length Ic of the short coherent light in the OCT scanning beam 21.

In the surgical microscope 16, there is a device 58 for controlling the OCT scanning beam 21 and for setting the position P of the object region volume 22 scanned by the OCT scanning beam 21 in the object region 18. The device 58 contains a computing unit 60. The computing unit 60 has an input interface 61 as a means for entering intended values and contains a computer program for controlling the OCT scanning beam 21 and adjusting the spatial extent and position P, that is, the position and orientation of the object region volume 22 scanned by the OCT scanning beam 21 in a coordinate system 62 that is stationary in relation to the apparatus. The computer program also serves to ascertain the position of the effective portion 26 in the scanned object region volume 22 by processing scanning information obtained by the OCT device 20 by scanning the object region volume 22.

The computing unit 60 comprises a program memory, which stores a model of the patient eye 14 in the form of CAD data, the CAD data being based on an examination of the object in a diagnostic apparatus not shown in any more detail here.

In the device 58, there is a function unit 64 comprising an image capturing device 66, by means of which the image 68 of the patient eye 14 may be captured in real time. The function unit 64 comprises a computing unit 69 comprising a program memory with a computer program which contains an image evaluation routine as image evaluation means. Proceeding from a reference image 70 of the patient eye 14, in which the position and orientation of the patient eye 14 is known in a coordinate system 72 which is fixed in relation to the surgical microscope 16 and hence to the OCT device 20, the image evaluation routine compares images 68 captured immediately in succession in real time by evaluating the structures of the sclera 74 and/or of the iris 76 of the patient eye 14 using the image capturing device 66 in order to specify, from this comparison, the position and orientation X, φ of the coordinate system 62 of the patient eye 14 in the object plane of the surgical microscope 16 in a coordinate system 72 that is fixed in relation to the surgical microscope 16 and hence to the OCT device 20. The program memory of the computing unit 60 further contains a computer program for controlling the OCT device 20 in order to determine the distance z of the patient eye 14 from the microscope main objective 42 by means of the OCT device 20 at regular time intervals. Hence, the computing unit 60 continuously also calculates the position of the coordinate system 72 that is fixed in relation to the patient eye 14 in the direction of the optical axis 82 of the microscope main objective 42 of the surgical microscope 16.

In the present case, the coordinate system 72 is a three-dimensional coordinate system. However, in an alternative advantageous embodiment of the invention, the coordinate system 72 may also be a two-dimensional coordinate system. In this case, the function unit 64 ascertains a displacement of the coordinate origin of the coordinate system 62 in the object plane of the surgical microscope 16 and a rotation of the coordinate system 62 about the optical axis 82 in the object plane perpendicular to the optical axis 82.

Further, the computer program in the program memory of the computing unit 60 contains a control routine which specifies the reference length for the OCT scanning beam 21 and the settings of the adjustable scanning mirrors 50, 52 for scanning the object region volume 22 in the object region with the patient eye 14. There is a control member 88, actuatable by an operator, in the device 58 for setting the object region volume 22 scanned by means of the OCT scanning beam 21.

The control member 88 is embodied as a 3D mouse, for example, as a 3Dconnexion SpaceNavigator 3D mouse by 3Dconnexion. The control member 88 comprises an operating element 96 movably mounted on a base 90 for movement in three translational 92a, 92b, 92c and/or three rotational 94a, 94b, 94c degrees of freedom of movement. The operating element 96 may be displaced relative to the base 90 by an operator using the fingers of one hand. In the process, a control signal $S_v$ is set for displacing the position P of the object region volume 22 scanned by the OCT scanning beam 21.

The device 58 for controlling the OCT scanning beam 21 contains a display unit 98, connected to the computing unit 60, in the form of a display for displaying a user interface, on which the object region volume 22 scanned on the patient eye 14 by means of the OCT scanning beam 21 is able to be visualized. Moreover, in the surgical system 10, the OCT scanning information for the OCT device 20 may be visualized for a surgeon in the eyepiece 46 of the surgical microscope 16 by means of a device for mirroring-in data 75.

Figure 3:
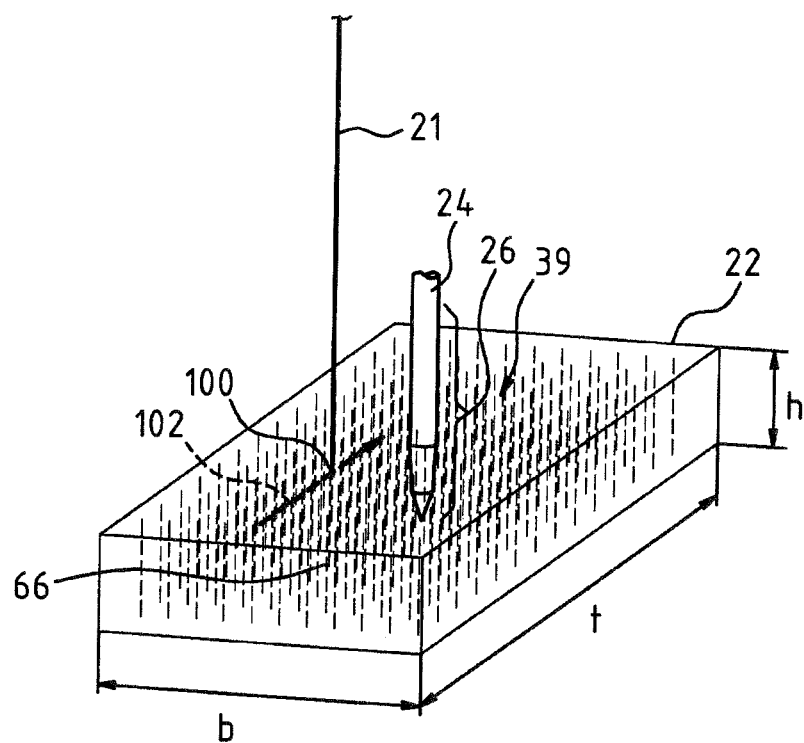
FIG. 3 shows an enlarged view of an object region volume scanned with an OCT scanning light beam from the OCT device.

FIG. 3 is an enlarged view of a cuboid object region volume 22 with the effective portion 26 of the surgical instrument 24. By way of example, the object region volume 22 has edges b, t, h with the following dimensions: b=3 mm, t=14 mm and h=2 mm.

Using the OCT scanning light beam, scattering centers scattering the OCT scanning light may be captured at a zone-shaped scanning location 100. The dimensions of the zones which are resolvable in an object with the OCT scanning light of an OCT system are of the order of the wavelength of the OCT scanning light. For the purposes of scanning the object region volume 22, the OCT scanning beam 21 is scanned and the reference length is changed in the OCT device 20. Here, the scanning location 100 is displaced in accordance with an object region volume scan 102. A control routine for scanning the object region volume 22 is combined with a program routine of the computer program which allows an operator to set the height h, the width b and the depth t of the object region volume 22 at an input interface 104 of the computing unit 60. Different profiles for the object region volume scan 102 may be set for the scanning locations 106 of the OCT scanning beam 21.

The object region volume 22 is visualized together with a model of the patient eye 14 on the display unit 98 by way of the computer program in the program memory of the computing unit 60. In the present case, this model of the object is a sphere with an arrow. This sphere corresponds to an eyeball of an average patient eye. Here, the arrow symbolizes the direction of view of the patient eye and indicates a position of the center of the cornea. The data in relation to the position and orientation of the patient eye 14, ascertained in the function unit 64, are fed to the computing unit 60. From this, the latter calculates display data for the model of the object in order thus to display, at the correct position, the scanned object region volume 22 (which is scanned by the OCT scanning beam 21 of OCT unit 20) set by means of the control routine on the basis of the ascertained position and orientation of the patient eye 14 in the coordinate system 72 that is stationary in relation to the surgical microscope 16, together with the position of the surgical instrument 24, which is calculated from the position of the marker 36, in a coordinate system 72 that is referenced to the surgical microscope 16.

Figure 4:
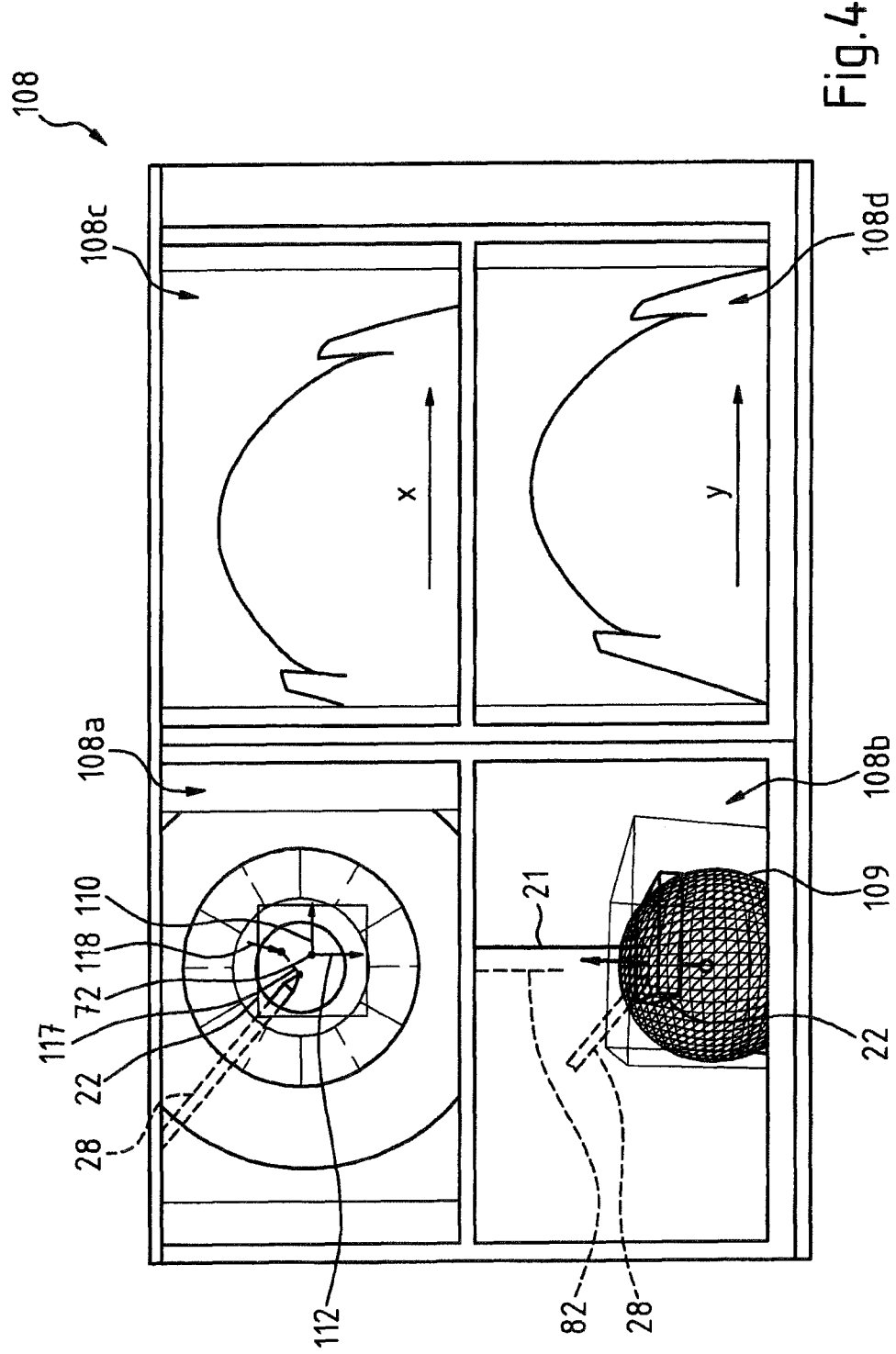
FIG. 4 shows a display window of a user interface of the surgical system.

FIG. 4 is an illustration of a user interface 108 of the display unit 98, in which there are display windows 108a, 108b, 108c and 108d. The display window 108a shows a view of the object region, captured by means of the image capturing device 66, with the object region volume 22 scanned by means of the OCT scanning beam 21 and a location of the needle body, which is determined from the portion of the marker 36 of the surgical instrument 24, in the coordinate system 72 that is fixed in relation to the surgical microscope 16.

The display window 108b visualizes a model 109 of the patient eye 14 in the coordinate system 72 that is fixed in relation to the surgical microscope 16, comprising the optical axis 82 of the microscope main objective 42 of the surgical microscope 16 and comprising the OCT scanning beam 21 in the coordinate system 72 that is fixed in relation to the apparatus. A so-called B-scan of the patient eye 14 with the OCT scanning beam 21 in the direction 110 identified in the display window 108a can be seen in the display window 108c. A B-scan of the patient eye 14 with the OCT scanning beam 21 in the direction 112 identified in the display window 108a is shown in the display window 108d.

A tracking operating mode may be set for the OCT device 20 by way of the computer program in the computing unit 60. In the tracking operating mode, the OCT scanning beam 21 follows the marker 36 in the effective portion 26 of the surgical instrument 24 if the latter is displaced on the patient eye 14. To this end, the OCT device 20 continuously obtains control signals from the computing unit 60, with information relating to the ascertained position of the effective portion 26. The position of the effective portion 26 of the surgical instrument 24 is visualized for a surgeon by means of the display windows 108a, 108b of the user interface of the surgical system 10.

Figure 5:
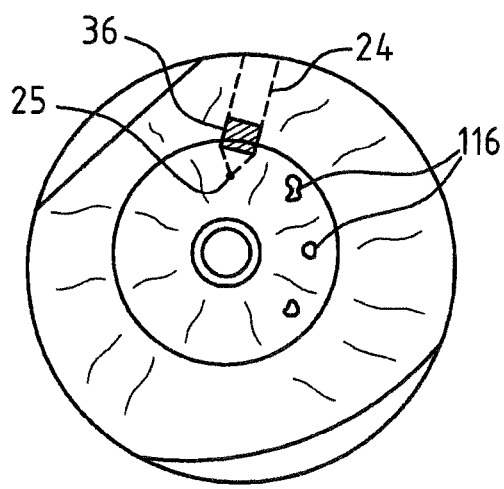
FIG. 5 shows a content of a display superposed on the image of the object region in the surgical microscope.

FIG. 5 shows the scanning information of the OCT device 20 visualized for a surgeon in the eyepiece 46 of the surgical microscope 16 by means of the device 75 for mirroring-in data, the scanning information being displayed by means of a display mirrored into the stereoscopic observation beam path 40. Using this, a position 25 of the surgical instrument 24, calculated in real time from the OCT scanning information, and the position of regions 116 of the cornea 12 of the patient eye 14 are visualized for the surgeon in a spatially correct superposition on the image of the patient eye 14.

An operator is able to enter intended values for the position of the effective portion 26 of the surgical instrument 24 at the input interface 61 of the computing unit 60, at which Descemet's membrane is intended to be separated from the remaining cornea 12 of the patient eye 14 by injecting air through the opening 32 of the needle body 28. On account of an entered intended value, the scanning information obtained by the OCT device 20 in respect of the object region volume 22 is compared with reference data. It should be noted that, as a matter of principle, an intended value may also be an information item about the patient eye 14 in diagnostic data obtained pre-surgery. The computer program in the computing unit 60 continuously ascertains deviation information about the spatial deviation of the effective portion 26 from the intended value when the surgical system 10 operates in the tracking operating mode. The deviation 117 of the effective portion 26 from the set intended value 118 is then displayed on the display window 108a and the display window 108b of the user interface 108 of the surgical system 10.

Thus, the surgical system 10 provides a surgeon with the information that the surgical instrument 24 is arranged at an intended position which corresponds to the set intended value for the effective portion 26 of the surgical instrument 24.

To this end, the surgical system 10 comprises an acoustic signal generator 121, which indicates arrival at an appropriate intended position to the surgeon if a norm, calculated in the computing unit 60, of the deviation of the effective portion 26 from the predeterminable intended value drops below a defined, adjustable threshold.

It should be observed that, alternatively or additionally, provision may also be made in a surgical system 10 according to the invention for the intended position of the effective portion 26 of the surgical instrument 24 being reached to be indicated by an optical and/or a haptic indication signal, for example a vibrating handle piece of the surgical instrument 24. In a further alternative embodiment of the surgical instrument 24, provision may be made for the computer program to generate a control signal from the deviation information, this control signal being fed to the surgical instrument 24, for triggering an instrument function if a trigger criterion is present.

Figure 6:
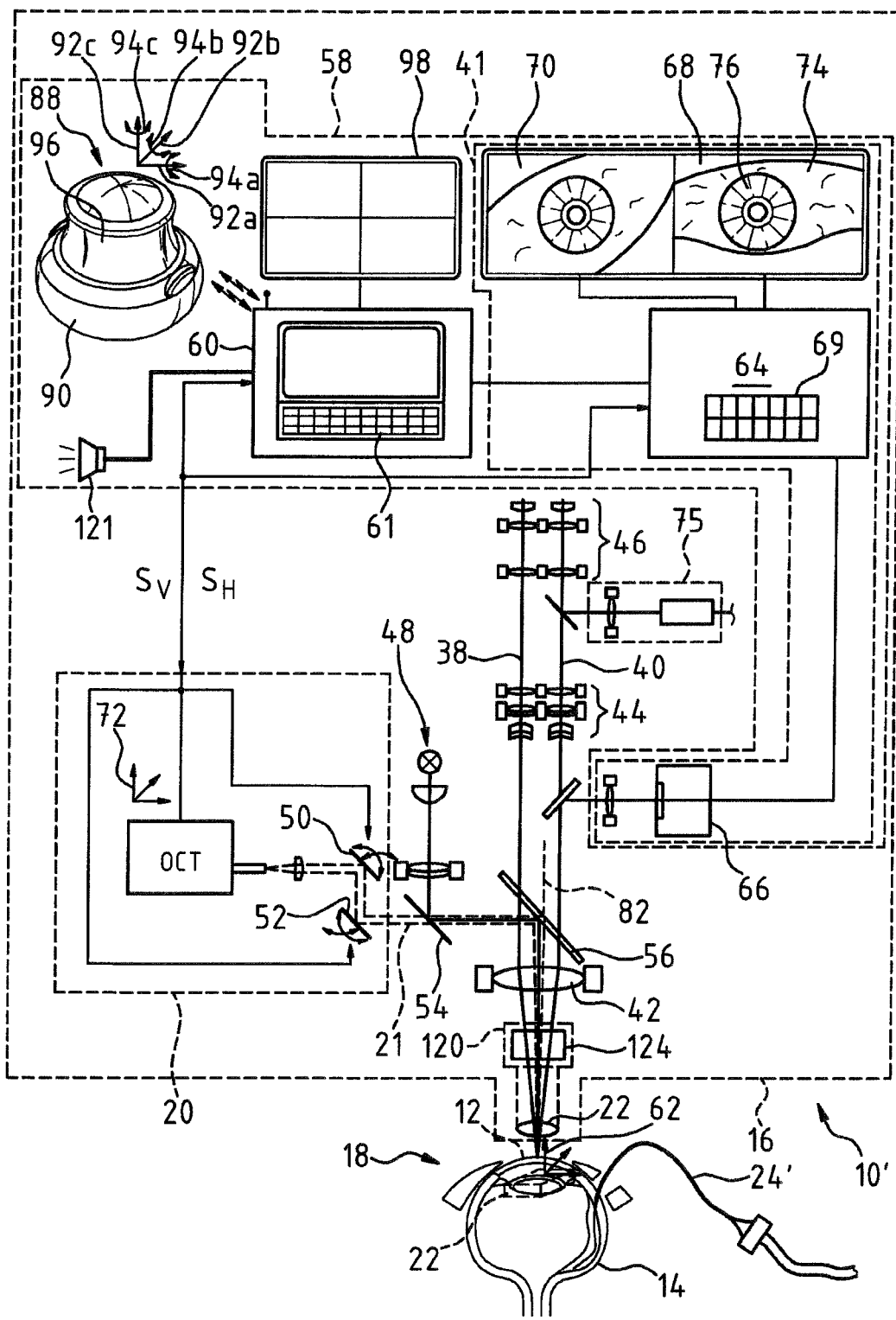
FIG. 6 shows a second surgical system for ophthalmic surgery, comprising a surgical microscope and OCT device, as well as a surgical instrument.

FIG. 6 shows a second surgical system 10' for ophthalmic operations, comprising a surgical microscope 16 and an OCT device 20, as well as a surgical instrument 24' for injecting stem cells into the retina 15 of the patient eye 14. To the extent that the components and elements of the surgical system 10' correspond to components and elements of the surgical system 10 described above, these are identified by the same numbers in the reference signs.

The surgical instrument 24' in the surgical system 10' is a micro-catheter which facilitates the discharge, accurate in terms of position, of stem cells at the retina 15 of the patient eye 14.

For the purposes of visualizing the retina 15 of the patient eye 14, the surgical microscope 16 in the surgical system 10' comprises an ophthalmoscopy attachment module 120 with an ophthalmoscopy lens 122 and a system for beam interchange and image erection 124, through which the stereoscopic observation beam path 38, 40 passes.

Figure 7:
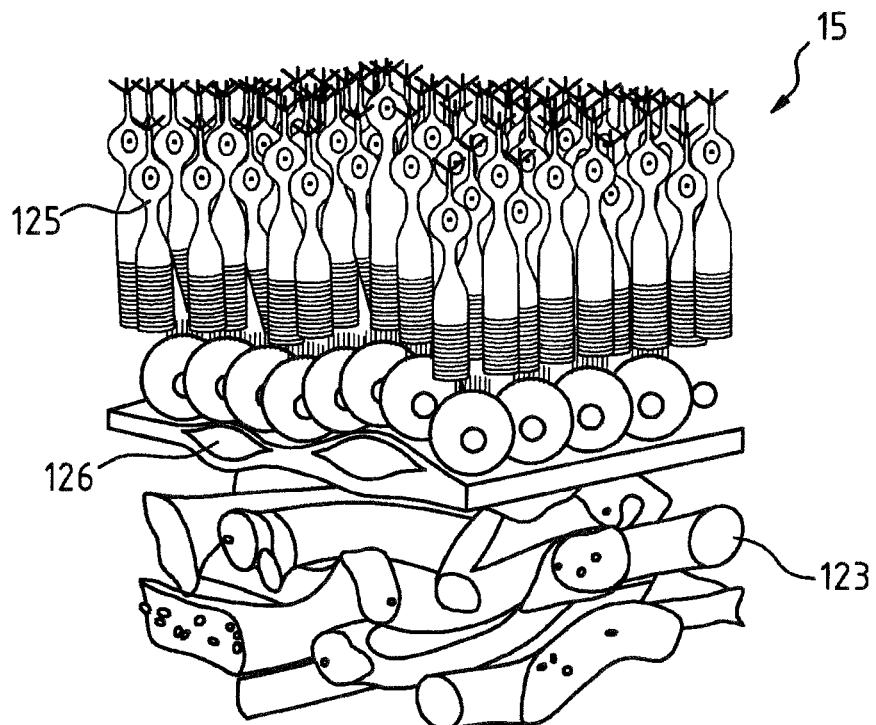
FIG. 7 is an enlarged partial view of the retina of a patient eye.

FIG. 7 is a magnified partial section of the retina 15 of the patient eye 14, comprising blood vessels 123 as well as photoreceptors 125 and drusen 126.

Figure 8:
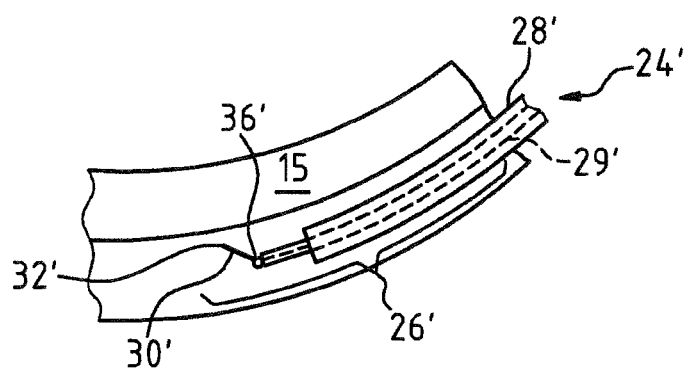
FIG. 8 is a partial view of the surgical instrument.

FIG. 8 shows a partial view of the surgical instrument 24' at the retina 15 of the patient eye. The surgical instrument 24' comprises an effective portion 26' at a catheter 28', extending in a longitudinal direction, with a capillary 29'. At the end of the catheter 28', there is an injection needle 30' with an opening 32' for discharging stem cells into the tissue of the retina 15. The catheter 28' consists of a material transparent to visible light, for example, mineral glass or PTFE. A marker 36' is formed at the end of the catheter 28'. The marker 36' is transparent to visible light. However, the spatial position of the marker 36' may be captured using the OCT scanning beam 21 of the OCT device 20.

Figure 9:
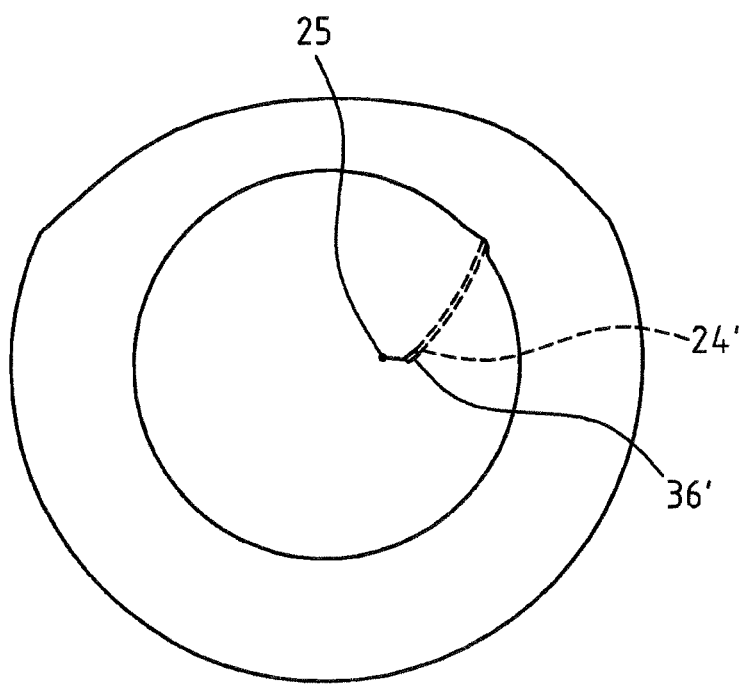
FIG. 9 shows a display window of a user interface of the surgical system.

FIG. 9 shows the scanning information of the OCT device 20 visualized for a surgeon in the eyepiece 46 of the surgical microscope 16 by means of the device 75 for mirroring-in data, the scanning information being visualized by means of a display mirrored into the stereoscopic observation beam path 40. Using this, a position 25 of the surgical instrument 24', calculated in real time from the OCT scanning information, and the position of the drusen 126 of the retina 15 are visualized for the surgeon in a spatially correct superposition on the image of the patient eye 14.

It should be observed that an apparatus according to the invention may also comprise combinations and sub-combinations of features of the embodiments described above. In particular, an apparatus according to the invention may be integrated not only into a surgical microscope, but also into an ophthalmoscope or any other examining device.

In summary, a system for performing a surgical procedure includes: an OCT device 20 for scanning an object region volume 22 disposed in an object region 18 with an OCT scanning beam 21; a control unit 58 for setting the position (P) of the object region volume 22 scanned by the OCT scanning beam 21 in the object region 18; a surgical instrument 24 having an effective section 26 arrangeable in the object region and localizable in the object region volume 22 with the OCT device 20; a computer unit 60 connected to the OCT device 20 and having a first computer program stored on a non-transitory computer readable medium and configured, when executed by a processor, to determine the position of the effective section 26 within the scanned object region volume 22 by processing scan information obtained with the OCT device 20 by scanning the object region volume 22; a second computer program stored on the non-transitory computer readable medium and configured, when executed by a processor, to compare the scan information to the reference data and being configured to provide a set value for the position of the effective section 26; the second computer program being configured for determining deviation information as to the spatial deviation of the effective section 26 from the set value; and, the second computer program being further configured to generate a control signal, which is supplied to the surgical instrument 24 to trigger a function of the surgical instrument 24, when a triggering criterion is present from the group: penetration depth of the effective section 26 of the surgical instrument 24 in body tissue or position of the effective section 26 of the surgical instrument 24 in the object region 18.

In conclusion, the following preferred features should, in particular, be retained. The invention relates to a surgical system 10, 10' comprising an OCT device 20 for scanning an object region volume 22 arranged in an object region 18 using an OCT scanning beam 21. The surgical system 10, 10' contains a device 58 for setting the position (P) of the object region volume 22 scanned by the OCT scanning beam 21 in the object region 18. The surgical system 10, 10' comprises a surgical instrument 24, 24' which comprises an effective portion 26, 26' which is arrangeable in the object region 18 and localizable in the object region volume 22 using the OCT device 20. In the surgical system 10, 10' there is a computing unit 60 connected to the OCT device 20, comprising a computer program for ascertaining the position of the effective portion 26, 26' in the scanned object region volume 22 by processing scanning information obtained by the OCT device 20 by scanning the object region volume 22.

It is understood that the foregoing description is that of the preferred embodiments of the invention and that various changes and modifications may be made thereto without departing from the spirit and scope of the invention as defined in the appended claims.

LIST OF REFERENCE SIGNS 10, 10' Surgical system
12 Cornea
14 Patient eye
15 Retina
16 Surgical microscope
18 Object region
20 OCT device
21 OCT scanning beam
22 Object region volume
24, 24' Surgical instrument
25 Position
26, 26' Effective portion
28 Needle body
28' Catheter
29, 29' Capillary
30 Tip
30' Hypodermic needle
32, 32' Opening
34 Handle piece
36, 36' Marker
38, 40 Stereoscopic observation beam path
42 Microscope main objective
44 Zoom system
46 Eyepiece
48 Illumination device
50, 52 Scanning mirror
54, 56 Beam splitter
58 Device
60, 69 Computing unit
61 Input interface
62, 72 Coordinate system
64 Function unit
66 Image capturing device
68 Image
70 Reference image
74 Sclera
75 Mirroring-in data
76 Iris
82 Optical axis
88 Control member
90 Base
92a, b, c Translational degrees of freedom
94a, b, c Rotational degrees of freedom
96 Operating element
98 Display unit
100 Scanning location
102 Object region volume scan
104 Input interface
106 Scanning locations
108 User interface
108a, 108b, 108c, 108d Display windows
109 Model
110, 112 Direction
116 Corneal region
117 Deviation
118 Intended value
121 Signal generator
120 Ophthalmoscopy attachment module
122 Ophthalmoscopy lens
123 Blood vessel
124 Beam interchange and image erection system
125 Photoreceptors
126 Drusen

What is claimed is:
1. A system for performing a surgical procedure, the system comprising:
an OCT device for scanning an object region volume disposed in an object region with an OCT scanning beam;

a control unit for setting the position (P) of the object region volume scanned by said OCT scanning beam in the object region;

a surgical instrument having an effective section arrangeable in the object region and localizable in the object region volume with said OCT device;

a computer unit connected to said OCT device and having a first computer program stored on a non-transitory computer readable medium and configured, when executed by a processor, to determine the position of said effective section within the scanned object region volume by processing scan information obtained with said OCT device by scanning the object region volume;

a second computer program stored on said non-transitory computer readable medium and configured, when executed by a processor, to compare said scan information to said reference data and being configured to provide a set value for said position of said effective section;

said second computer program being configured for determining deviation information as to the spatial deviation of said effective section from said set value; and, said second computer program being further configured to generate a control signal, which is supplied to said surgical instrument to trigger a function of said surgical instrument, when a triggering criterion is present from the group: penetration depth of said effective section of said surgical instrument in body tissue or position of said effective section of said surgical instrument in the object region.

2. The system of claim 1, wherein said effective section has a capillary defining an opening for discharging a medium into the object region.

3. The system of claim 2, wherein said effective section is made, at least in part, of a material transparent for visible light.

4. The system of claim 3, wherein said effective section is provided with a marker localizable with said OCT scanning beam.

5. The system of claim 1, wherein a tracking operating mode is adjustable with one of said first and second computer programs in said computer unit by virtue of the OCT device continuously receiving control signals with information from said computer unit for the purposes of tracking the effective section of said surgical instrument.

6. The system of claim 5, wherein said information includes the most recently ascertained position of the effective section.

7. The system of claim 1, wherein said reference data are preoperatively obtained diagnostic data.

8. The system of claim 1, further comprising:
an input interface for providing said set value for said position of said effective section in the object region volume; and,
said input interface being configured for manually inputting said set value.

9. The system of claim 8, further comprising a device for providing a position display signal in dependence upon the determined deviation of said effective section from said set value.

10. The system of claim 9, wherein said device provides said position display signal when a standard deviation of said effective section from the pregiven set value drops below a defined limit value.

11. The system of claim 10, wherein said limit value is adjustable.

12. The system of claim 11, wherein said position display signal is an acoustic or an optic or a touch display signal.

13. The system of claim 1, further comprising a visualization unit for visualizing the position of said effective section of said surgical instrument in the object region for an observing person.

14. The system of claim 1, further comprising a surgical microscope to provide an image of the object region with magnification.

15. A method for operating a surgical instrument having an effective section, the surgical instrument including a computer having a non-transitory computer readable memory whereon a computer program is stored and the method comprising the following steps:
arranging the effective section of said surgical instrument in an object region volume in an object region;
providing a desired value for the position of the effective section in the object region volume;
comparing, via the computer program, scan information, which is obtained from an OCT device, with reference data;
determining, via the computer program, deviation information as to the spatial deviation of the effective section from the set value;
generating, via the computer program, a control signal from the deviation information for triggering an instrument function of the surgical instrument when a triggering criterion is present from the group: penetration depth of said effective section of said surgical instrument in body tissue or position of said effective section of said surgical instrument in the object region; and,
supplying the control signal to the surgical instrument.

16. The method of claim 15, comprising the further step of discharging a medium into the object region with the surgical instrument.

* * * * *

UNITED STATES PATENT AND TRADEMARK OFFICE
CERTIFICATE OF CORRECTION

PATENT NO. : 10,682,051 B2
APPLICATION NO. : 15/481381
DATED : June 16, 2020
INVENTOR(S) : Matz et al.

Page 1 of 1

It is certified that error appears in the above-identified patent and that said Letters Patent is hereby corrected as shown below:

On page 2:
Under "OTHER PUBLICATIONS": delete
"doktors-der-humanbiologie-des-fachbereichs-medizin-der-
justusliebig-universitaet-giessen.html" and substitute
-- doktors-der-humanbiologie-des-fachbereichs-medizin-der-justus-
liebig-universitaet-giessen.html -- therefor.

In Column 8:
Line 32: delete "b=3 mm" and substitute -- b≈3 mm -- therefor.
Line 33: delete "t=14 mm" and substitute -- t≈14 mm -- therefor.
Line 33: delete "h=2 mm" and substitute -- h≈2 mm -- therefor.

Signed and Sealed this
First Day of September, 2020

Andrei Iancu
*Director of the United States Patent and Trademark Office*